United States Patent [19]
Schramm et al.

[11] Patent Number: 5,284,156
[45] Date of Patent: Feb. 8, 1994

[54] AUTOMATIC TISSUE SAMPLING APPARATUS

[75] Inventors: John B. Schramm; Anton Mittermeier, both of Skokie, Ill.

[73] Assignee: M3 Systems, Inc., Northbrook, Ill.

[21] Appl. No.: 753,602

[22] Filed: Aug. 30, 1991

[51] Int. Cl.⁵ .............................................. A61B 10/00
[52] U.S. Cl. .................................... 128/754; 606/171
[58] Field of Search ................ 128/754, 753, 751, 749; 606/167, 168, 170, 171, 182, 184

[56] References Cited

U.S. PATENT DOCUMENTS

| | | | |
|---|---|---|---|
| 4,600,014 | 7/1986 | Beraha | 128/754 |
| 4,699,154 | 10/1987 | Lindgren | 128/754 |
| 4,776,346 | 10/1988 | Beraha et al. | 128/754 |
| 4,944,308 | 7/1990 | Akerfeldt | 128/751 |
| 4,953,558 | 9/1990 | Akerfeldt | 128/751 |
| 4,958,625 | 9/1990 | Bates et al. | 128/754 |
| 4,976,269 | 12/1990 | Mehl | 128/754 |
| 4,991,600 | 2/1991 | Taylor | 128/754 |
| 5,025,797 | 6/1991 | Baran | 128/754 |

FOREIGN PATENT DOCUMENTS

| | | | |
|---|---|---|---|
| 318447 | 5/1989 | European Pat. Off. | A61B 10/00 |
| PCTSE83001-12 | 10/1983 | PCT Int'l Appl. | A61B 10/00 |
| 8600755 | 2/1986 | Sweden . | |
| 483829 | 2/1970 | Switzerland | A61B 10/00 |

OTHER PUBLICATIONS

Bard Radiology Brochure, 1987, Author unknown, 2 pages.

*Primary Examiner*—Stephen C. Pellegrino
*Assistant Examiner*—Guy V. Tucker
*Attorney, Agent, or Firm*—Dick and Harris

[57] ABSTRACT

An apparatus for the automated and facilitated handling and operation of a biopsy needle system, having a first inner needle component and a second outer needle component. The first inner and second outer needles are provided with first and second handles, respectively, which are fitted into first and second yokes of the apparatus. The apparatus is configured to maintain the first inner and second outer needles in a first position, during insertion of the biopsy needle point into the tissue being sampled. The apparatus is further configured to move the first inner and second outer needles into second and third positions, respectively, in rapid, automated succession so as to segment and enclose a tissue sample, which may be tested after removal of the biopsy needle system from the tissue. A tissue sample inspection feature permits facilitated repositioning and maintenance of the first inner needle relative to the second outer needle after retrieval of the tissue sample to, in turn, enable inspection of the retrieved tissue sample without removal of either needle from the apparatus.

23 Claims, 3 Drawing Sheets

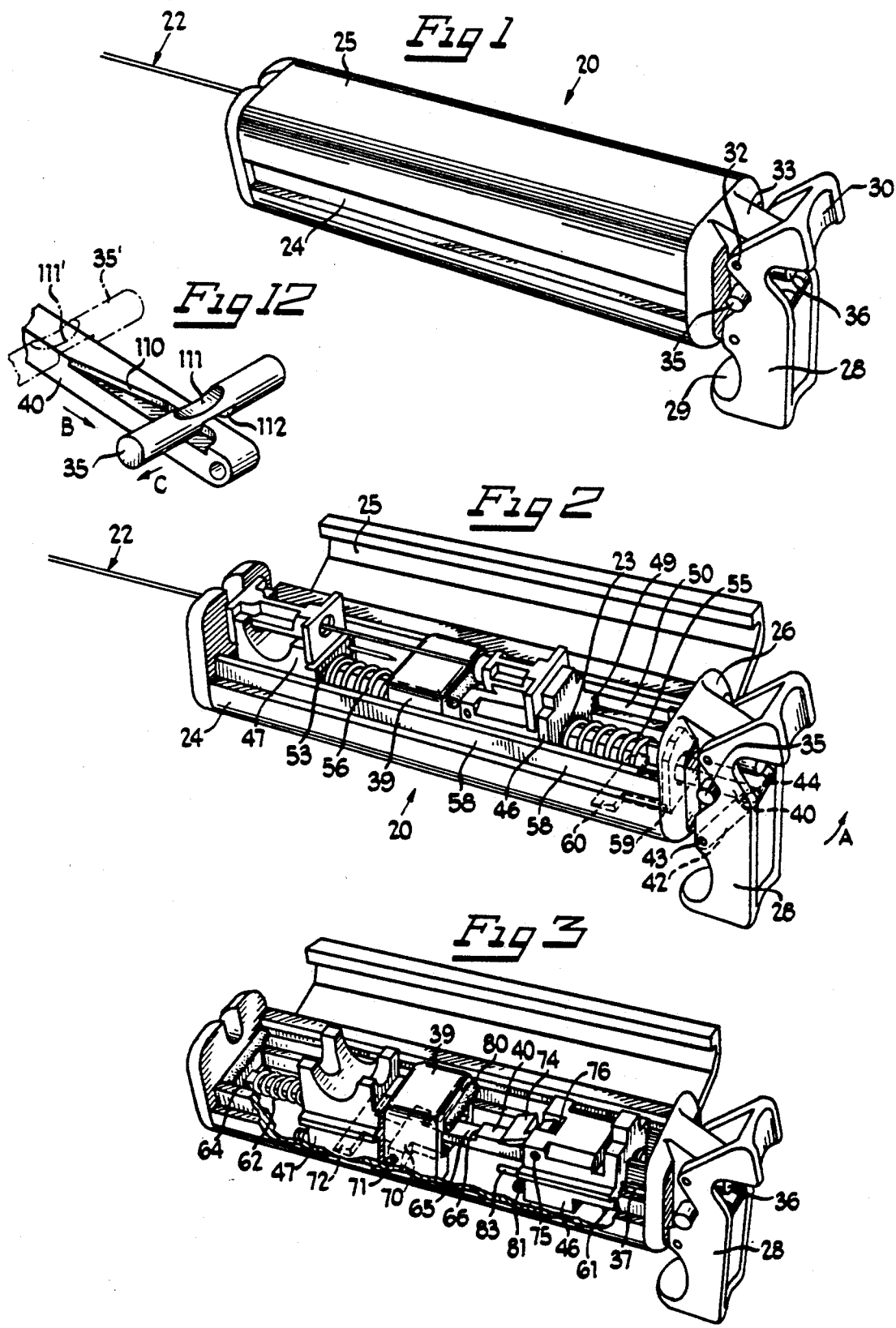

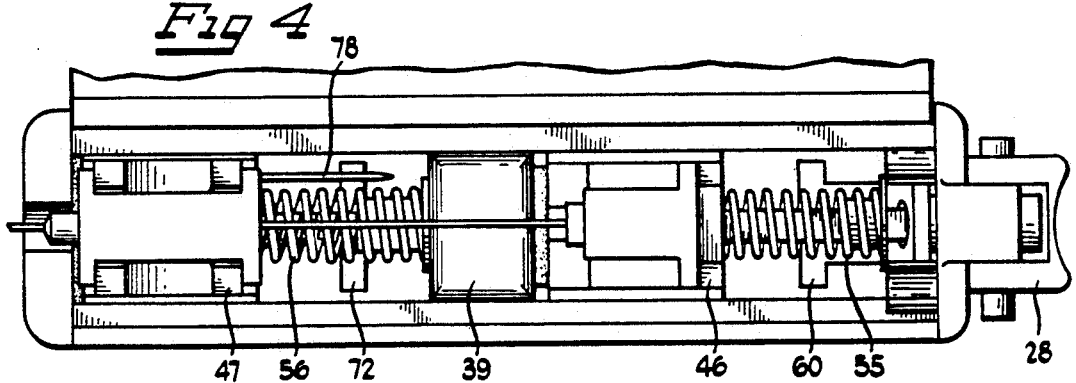
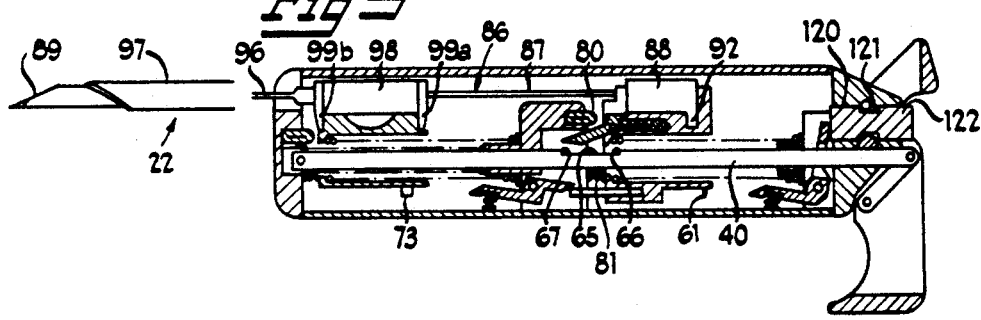
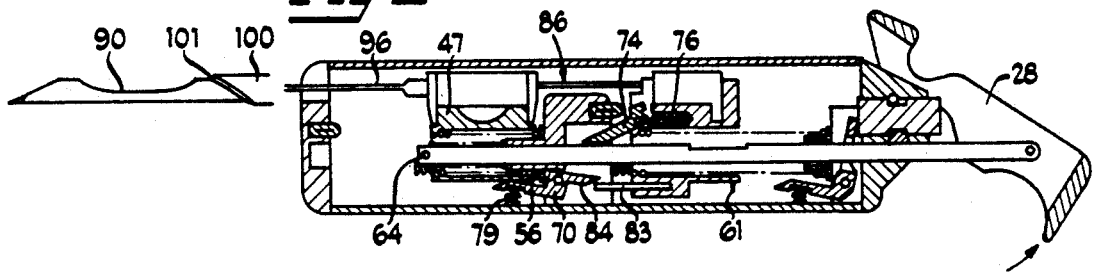
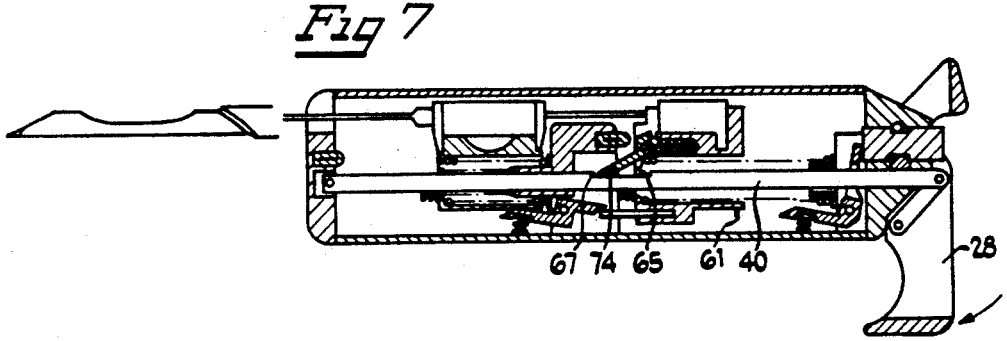

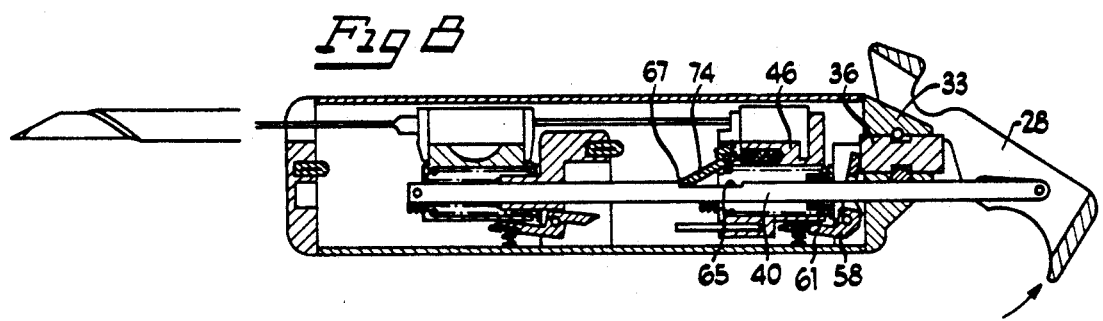
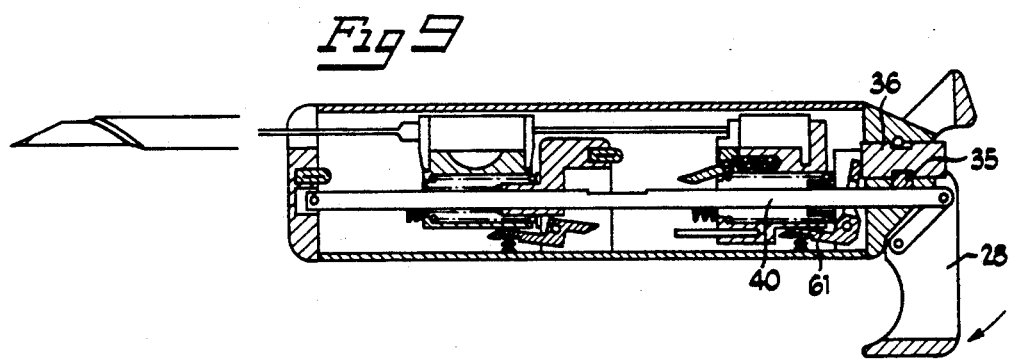
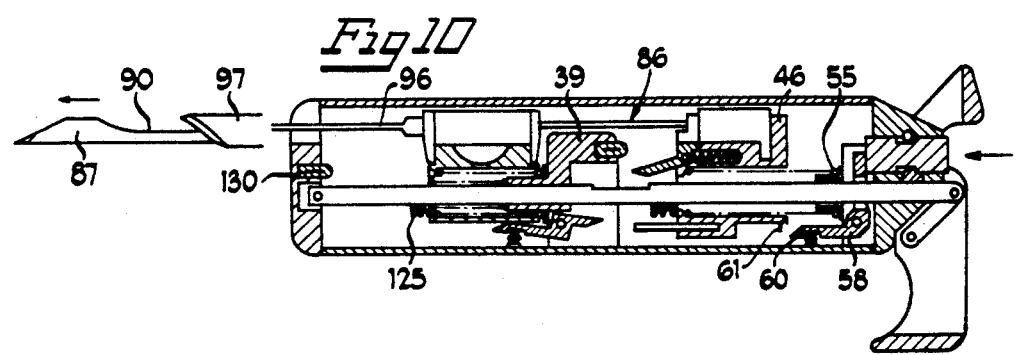
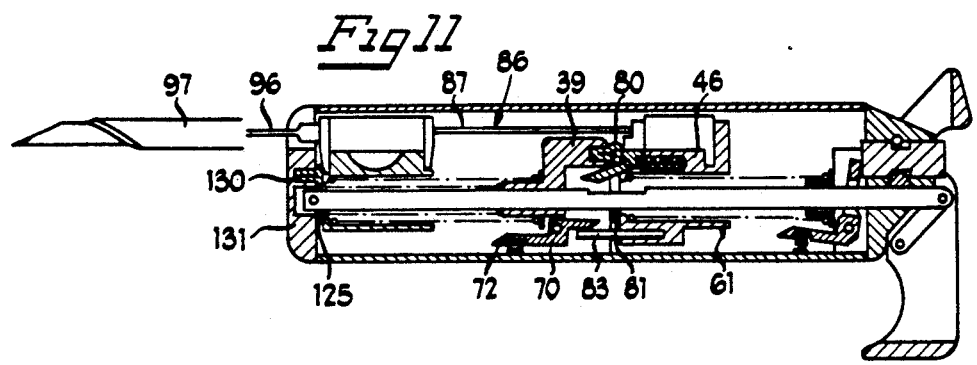

AUTOMATIC TISSUE SAMPLING APPARATUS

BACKGROUND OF THE INVENTION

The present invention relates to tissue sampling devices associated with biopsy needles, and in particular, to an automatic tissue sampling apparatus for utilizing two-piece biopsy needle systems for facilitating the retrieval of a tissue sample for testing.

A typical biopsy needle system utilized in obtaining tissue samples is composed of two parts, a first inner needle and a second outer needle. The first inner needle consists of a substantially solid shaft, having a first handle disposed at one end. A cutting point, to facilitate insertion of the needle into the tissue to be sampled, is located at the other end of the shaft, opposite to the position of the handle. Positioned proximate to the cutting point, is a tissue holding region, which is in the form of a cut-out region or flat in the otherwise substantially cylindrical shaft.

The second outer needle is typically hollow. At one end a second handle is disposed. The hollow passageway extends through the second handle, to enable the solid shaft of the first inner needle to be inserted into the passageway and into and through the entire hollow shaft of the second outer needle.

The shaft of the first inner solid needle is typically greater in length than the entire second outer hollow needle structure. When the first and second handles are placed in a particularly spaced co-axial configuration, the hollow shaft of the second outer needle covers the tissue holding region of the first inner needle. The tissue holding region may be exposed by projecting the first inner needle further into the second outer needle, bringing the first and second handles closer together.

To obtain a tissue sample, the biopsy needle is typically inserted into a patient, into the specific tissue to be sampled, at the desired cell mass to be investigated, with the first inner and second outer needles relatively positioned in the first described configuration, so that the tissue holding region is covered. The tissue holding region is then exposed, by the operator holding the second handle of the second outer needle stable while projecting the first inner needle forward a short distance along its sharp pointed region—until a portion of the tissue being tested surrounds the flat cut-out of the tissue holding region.

The second outer needle, which also has a sharp, though hollow, point disposed at the end of the hollow shaft opposite the second handle, is then moved forward, relative to the now-stabilized first inner needle—to cut off the tissue sample from the rest of the tissue, and cover the tissue sample about the flat cut-out of the tissue holding region. The angled cutting point of the second outer needle serves to sever the tissue sample. The first inner and second outer needles are typically maintained in a particular angular concentric orientation with respect to one another, prior to insertion, so as to maintain the forwardmost portion of the second outer needle point centered when positioned over the flat, cut-out region of the first inner needle.

After the tissue is severed and confined between the first inner and second outer needles, the inner and outer needles will be brought back to the same relative positions they occupied immediately prior to initial insertion of the biopsy needle system into the patient. To prevent loss or contamination of the tissue sample, the first inner and second outer needles are typically removed from the patient in this tissue-isolating configuration.

As the configuration of the first inner and second outer needles, utilized for initial insertion, and final removal from the patient, requires that the first and second handles be spaced apart in a particular configuration, the manual manipulation of such a biopsy needle system requires considerable dexterity, concentration and skill on the part of the operator. The concentration necessary to maintain the proper spacing may detract from the concentration necessary to make insertion and removal of the biopsy needle as painless as possible for the patient. Accordingly, it is desirable to provide a form of automatic tissue sampling apparatus, which accomplishes some, if not all of the handling steps just described—so that the operator may be concerned with the crucial initial step of insertion and final step of removal, of the biopsy needle; to reduce the amount of discomfort to the patient, to improve the quality of the results of the tissue sampling procedure, and to enhance the successful repeatability of the procedure, from one patient to the next.

Examples of prior art automatic tissue sampling apparatus include those disclosed in PCT application No. PCT/SE83/00112, Swedish Patent No. 8600755, U.S. Pat. No. 4,699,154, issued to Lindgren, EPO Application No. 0 318 447 and Swiss Patent No. 483 829.

In the PCT application, an automatic tissue sampling apparatus is disclosed, in which the first inner needle of the biopsy needle is propelled forward by a pressure plate which is driven by a compressed spring, and the second outer needle is propelled by a movable slide which receives the second handle of the second outer needle. The movable slide for holding the second outer needle is also propelled by a compressed spring. In order to prepare the apparatus for use, each of the springs and respective slides must be cocked separately, either manually or through the use of a specially shaped tool. The slide for the outer handle is held in place by a catch which is configured to be released upon contact with a projection arranged upon the slide for the first handle of the first inner needle. The pressure plate for the first handle of the first inner needle is in turn retained in its cocked position by a trigger which is actuatable by the operator. While it is possible to cock each of the springs, with the biopsy needle already in place, it is contemplated that such cocking will take place well prior to loading of the needle.

In operation then, once the springs have been cocked and the biopsy needle has been loaded, the operator inserts the needle into the tissue to be sampled, as previously described. He or she may then depress the trigger which releases the spring for propelling the first inner needle. As the first inner needle is moved forward, the pressure plate releases the retaining mechanism which has been previously holding the movable slide for the second handle of the second outer needle. The second outer needle is thus moved forward shortly after the first inner needle, completing the sampling movement. The trigger in the apparatus is biased by a spring into position to retain the compressed spring for the first inner needle slide, and is configured to provide increasing resistance to depression, up until a predetermined position, at which point, the resistance is sharply increased and further depression results in the immediate release of the compressed spring. No means are provided for preventing inadvertent actuation of the automatic tissue sampling apparatus. Due to the inherent hazardous nature of the extremely sharp points of the biopsy needle and the power of the springloaded mechanism, it is desirable, therefore, to provide a tissue sampling apparatus which has an automatically engaging safety mechanism, which must be consciously overcome before the tissue sampling apparatus may be actuated. In addition, it may be often awkward and/or difficult to manually overcome the force of the uncompressed springs which drive the movable slides. Accordingly, it would be desirable to provide an automatic tissue sampling apparatus which may be readily prepared for use, immediately before insertion, without the need for extreme physical exertion or the use of awkward and/or specially configured tools.

The tissue sampling device embodied in U.S. Pat. No. 4,699,154 to Lindgren discloses a housing in which two slides are mounted for longitudinal movement, the slides being configured to receive the first and second handles of the first inner and second outer needles, respectively. Each of the slides is propelled by a pair of compressed springs. The rearward slide, for propelling the handle of the first inner needle, is propelled by springs which bear against a rear wall of the housing. The slide for the handle of the second outer needle is propelled by compressed springs which bear against a fixed, transversely-extending wall arranged in the housing between the forward and rear slides. Both of the slides are arranged to have a guide member extending through them. A drawbolt is operably associated with each of the slides for limited axial movement relative thereto, such that when the drawbolt is pulled backward, both of the slides are simultaneously drawn against the bias of the respective springs, to a cocking position. When the cocking position is reached, retaining members associated with each of the slides engage the respective slides to retain them in their cocked positions.

In a manner similar to that discussed with regard to the PCT application, an external triggering mechanism is provided, which is actuatable by the operator to release the retaining mechanism for the slide for the first inner needle. Once the slide for the first inner needle has been propelled forward, a predetermined distance, a projection on the first slide releases the retaining mechanism for the slide for the handle of the second outer needle; enabling it to be propelled forward by its respective springs.

One possible drawback to the tissue sampling apparatus of the Lindgren '154 patent is that it is configured so that both sets of springs are compressed, and the slides brought into their retained positions by a single pulling motion upon the drawbolt. Accordingly, the combined strengths of all of the springs must be overcome in order to cock the mechanism. Due to the substantial power stored in the springs which is necessary for the rapid operation of the tissue sampling apparatus, it may be difficult for certain operators to rapidly and easily operate the cocking mechanism. Accordingly, it would be desirable to provide an automatic tissue sampling apparatus with a built-in cocking mechanism which is readily and easily operated, and which does not require substantial strength or effort in order to arm the apparatus.

The tissue sampling device of the Lindgren '154 patent is also provided with a safety mechanism, for precluding inadvertent actuation. However, the safety mechanism is configured such that it must be positively engaged by the operator, in order to place the tissue sampling apparatus into condition that it cannot be accidentally fired. Accordingly, the effectiveness of the safety device is dependent upon the operator remembering to set the safety. It would be more desirable to provide an automatic tissue sampling apparatus which is configured with a safety device which engages automatically upon the cocking of the apparatus, and is thereby not dependent upon the operator's remembering to engage the safety. Rather, it would be desirable to configure the safety device so the operator must affirmatively disengage the safety before the tissue sampling apparatus can be actuated.

Swiss Patent No. 483 829 discloses a "gun"-shaped automatic tissue sampling apparatus, in which the springs are cocked by direct pulling force, and so suffers from the same potential drawback of requiring substantial difficulty and effort to arm the device.

EPO Application No. 0 318 447 discloses a purportedly disposable automatic tissue sampling apparatus, in which the springs for the slides for the first inner and second outer needles are simultaneously cocked by rotating an outer sleeve backward, against the force of both springs. Tabs on the slides ride on cam surfaces to force the slides backward against the springs requiring substantial effort to operate.

In addition to the foregoing, it is well known that often during tissue sampling procedures, the quality and/or quantity of the tissue being sampled may vary from procedure to procedure. Accordingly, it is desirable to provide a means for permitting inspection of the tissue sample, without removing the biopsy needle components from the tissue sampling apparatus. In that way, should the size or quality of the sample be inadequate, the biopsy needle may be reinserted into the very same patient for another attempt at obtaining a suitable sample. Such a sample inspection procedure would also permit access to the sample for subsequent deposit of same onto a microscope slide or other sample holding apparatus for further processing of the tissue sample.

Such prior art tissue sampling apparatus such as those disclosed in the PCT application and in the Lindgren '154 patent are known to be large, relatively heavy and complicated devices, which are also relatively costly.

It is thus an object of the present invention is to provide an improved automatic tissue sampling apparatus which is easy to load and bring into readiness for use, without undo exertion and/or complicated manipulation of its components; while providing a facilitated, positive locking, tissue sample inspection capability.

It is a further object of the invention to provide an automatic tissue sampling apparatus which is provided with an automatically engaging safety device, which does not rely upon the operator for its effectiveness and which must be affirmatively disengaged before the tissue sampling apparatus may be actuated.

The present invention seeks, as another goal, the provision of an automatic tissue sampling apparatus which is less complicated and therefore easier and less expensive to construct, and which has a lighter construction for greater ease of operation and manipulation.

Yet another goal of the invention is to provide an automatic tissue sampling apparatus which is provided with various internal shock and sound absorbing means so as to render the apparatus quieter and less jarring in operation, so as to decrease the actual and/or perceived discomfort of the patient during the tissue sampling procedure; while ensuring better practitioner accuracy during the procedure.

These and other objects and goals of the invention will become apparent and light of the present specification, drawings and claims.

SUMMARY OF THE INVENTION

The present invention is directed to an automatic tissue sampling apparatus, for use with a biopsy needle system of the kind including a first inner needle (first needle) having a shaft member and two ends, a first handle disposed at one of the shaft member, a cutting point disposed at the other end of the shaft member, and a tissue holding region positioned between the cutting point and the first handle, and a second outer needle (first needle) having a hollow shaft, a second handle with a passageway arranged therethrough for reciprocation of the first inner needle, and particularly for the automated and facilitated handling and operation of the double needle biopsy needle system during a biopsy procedure.

The automatic tissue sampling apparatus comprises a housing means which has a forward region, a rearward region, a longitudinal axis and a transverse axis. First inner needle transport means (first transport means) are operably disposed in the housing means, for reciprocating movement between a first forward position (first transport means forward position) and a second retracted position (first transport means retracted position) therewithin the rearward region, in a direction substantially parallel to the longitudinal axis of the housing means. Second outer needle transport means (second transport means) are operably disposed in the forward region of the housing means for reciprocating movement between a third forward position (second transport means forward position) and a fourth, retracted position (second transport means retracted position) therewithin the forward region, in a direction substantially parallel to the longitudinal axis of the housing means. The first inner needle transport means and the second outer needle transport means are configured to receive and longitudinally move in the reciprocating directions, the first handle of the first inner needle and the second handle of the second outer needle, respectively.

First biasing means are operably arranged in the rearward region of the housing means for biasing the first inner needle transport means, and, in turn, the first inner needle forwardly toward the first position, within the rearward region. The second biasing means are operably arranged in the forward region of the housing means, for biasing the second outer needle transport means, and, in turn, the second outer needle forwardly toward the third forward position, within the forward region.

Cocking means, integrally and operably associated with the first inner needle transport means and the second outer needle transport means, draw the first inner needle transport means, and, in turn, the first inner needle transport means, rearwardly into the second retracted position thereof, within the rearward region, and also draw the second outer needle transport means, and, in turn the second outer needle, rearwardly into the fourth, retracted position thereof, within the forward region.

First transport retaining means, operably associated with the first inner needle transport means, releasably retain the first inner needle transport means in the second retracted position. Second transport retaining means, operably associated with the second outer needle transport means, releasably retain the second outer needle transport means in the fourth, retracted position.

First release means, are operably associated with the first transport retaining means, actuate the first transport retaining means to release the first inner needle transport means from the second retracted position to, in turn, enable the first inner needle transport means to be driven rapidly forward by the first biasing means, toward the first position thereof. Second release means are operably associated with the second transport retaining means, to actuate the second transport retaining means to release the second outer needle transport means, when the first inner needle transport means substantially arrives at the first forward position thereof, to, in turn, enable the second outer needle transport means to be driven forward by the second biasing means.

The preferred embodiment of the invention also includes automatic tissue sample inspection means which enable the facilitated reorientation of the second outer needle transport means relative to the first inner needle transport means, after removal of the biopsy needle system from the tissue being sampled; with the first inner needle transport means, and, in turn, the first inner needle, in its first forward position in the rearward region, and with the second outer needle transport means, and the second outer needle, repositioned in the fourth retracted position—thereby exposing the tissue holding region and the sampled tissue which had been removed as a result of the tissue sampling procedure. The automatic tissue sample inspection means cooperates with the second transport retaining means to releasably, yet positively maintain the second outer needle transport means in the fourth retracted position; to expose the tissue holding region with its removed sample of tissue.

Preferably, the automatic tissue sample inspection means comprises a detent member which is operably disposed on the first inner needle transport means to disengage the first inner needle transport means from the cocking means. An engagement member, operably disposed on the second outer needle transport means, places the detent member, which is normally biased into a disengaged position relative to the cocking means, into engagement with the cocking means, when the second outer needle transport means is in the fourth, retracted position. The cocking means and the first inner needle transport means and the second outer needle transport means are operably configured such that upon a first actuation of the cocking means after removal of the biopsy needle system from the tissue being sampled, the second outer needle transport means may be drawn to the fourth, retracted position within the forward region and is retained by the second transport retaining means. The engagement member places the detent member into engagement with the cocking means, and upon a second consecutive actuation of the cocking means, the first inner needle transport means is drawn into the second, retracted position, within the rearward region, and retained by the first transport retaining means. At that time, re-sampling of the tissue, if necessary, may be accommodated.

The housing means comprises a substantially solid-walled, generally continuous apparatus enclosure having a substantially rectangular cross-sectional configuration for substantially enclosing all of the moving portions of the automatic tissue sampling apparatus to protect it from dirt, moisture and the like, as well as to provide audio isolation of the moving portions while reducing noise produced during operation of the apparatus. The housing means are formed by two oppositely disposed sidewalls which extend substantially parallel to the longitudinal axis. Each of the sidewalls has a forward end and a rearward end. A forward wall extends substantially parallel to the transverse axis and operably connects the forward ends of the sidewalls. A rearward wall extend substantially parallel to the transverse axis and operably connects the rearward ends of the sidewalls. A central support member is operably positioned between the sidewalls and substantially centrally between the forward and rearward walls. A bottom wall further helps to enclose the moving portions of the apparatus, while an openable cover permits the installment and removal of a biopsy needle system, yet provides full enclosure of its elements during the biopsy procedure.

In the preferred embodiment of the invention, the first and second biasing means are operably disposed and configured to function substantially independently of each other.

Safety means additionally may be operably associated with at least the first release means and the cocking means to preclude inadvertent actuation of the automatic tissue sampling apparatus, once it has been cocked. The safety means preferably comprises a stop member, which is operably configured to be automatically deployed and removably positioned to physically preclude actuation of at least the first release means, upon and by actuation of the cocking means.

The first inner needle transport means preferably comprises a first yoke member, which is longitudinally slidably retained in the rearward region, between the sidewalls, the rearward wall and the central support member. The first yoke member receives and retains the first handle of the first inner needle. The second outer needle transport means similarly comprises a second yoke member, which is longitudinally slidably retained in the forward region, between the sidewalls the forward wall and the central support member, and is operably configured to receive and retain the second handle of the second outer needle.

In the preferred embodiment of the invention, the first biasing means is a compressed spring, operably positioned between the rearward wall and the first yoke member. Likewise, a compressed spring, operably positioned between the central support member and the second yoke member, forms the second biasing means.

The cocking means preferably includes a shaft which extends substantially parallel to the longitudinal axis and is operably disposed for reciprocating movement parallel to the longitudinal axis. The shaft has two opposite ends, the first of which extends through an aperture in the rearward wall. A lever which is disposed upon the rearward wall for pivotal movement around an axis extending substantially parallel to the transverse axis, is operably associated with the first end of the shaft such that when the lever is pivotally moved, the shaft is moved rearwardly. A cross member, operably disposed upon the second end of the shaft, abuts a forward face of the second yoke member, so that when the lever is actuated and the second yoke member is in the third position, the cross member draws the second yoke member toward the fourth position.

In a preferred embodiment of the invention, a first actuation of the cocking means moves the second outer needle transport means to the fourth, retracted position. A second, successive actuation of the cocking means orients the first inner needle transport means to the second, retracted position, bringing the apparatus into readiness for insertion of the biopsy needle system into the tissue to be sampled.

BRIEF DESCRIPTION OF THE DRAWINGS

FIG. 1 is a perspective view of the automatic tissue sampling apparatus, according to the preferred embodiment of the invention, having a double needle, biopsy needle system loaded therein;

FIG. 2 is a perspective view of the apparatus, according to FIG. 1 with the cover opened to show how the biopsy needle system is loaded into the apparatus;

FIG. 3 is a perspective view of the apparatus, according to FIG. 2, showing, in partial cutaway, further details of the construction of the apparatus;

FIG. 4 is a top plan view of the apparatus, according to FIG. 2;

FIG. 5 is a side elevation, in section, of the apparatus, with a biopsy needle system loaded therein, in its initial configuration prior to cocking, further showing, in enlargement, the relative positions of the needles;

FIG. 6 is a side elevation, in section, showing the apparatus according to FIG. 5 during the first cocking stroke, further showing, in enlargement, the relative positions of the needles;

FIG. 7 is a side elevation, in section, of the apparatus according to FIG. 5, showing the apparatus upon completion of the first cocking stroke and release of the cocking elements immediately thereafter, further showing, in enlargement, the relative positions of the needles;

FIG. 8 is a side elevation, in section, of the apparatus according to FIG. 5, shown during the second cocking stroke further showing, in enlargement, the relative positions of the needles;

FIG. 9 is a side elevation, in section, of the apparatus according to FIG. 5, shown fully cocked, after release of the cocking elements, and ready for insertion of the biopsy needle system into the tissue to be sampled, further showing, in enlargement, the relative positions of the needles;

FIG. 10 is a side elevation, in section, of the apparatus according to FIG. 5, shown immediately after the button has been depressed, further showing, in enlargement, the relative positions of the needles;

FIG. 11 is a side elevation of the apparatus, in section, according to FIG. 5, showing the apparatus after firing but before the yokes have returned to their initial positions, equivalent to the positions prior to cocking, further showing, in enlargement, the relative positions of the needles; and FIG. 12 is a schematic perspective view, illustrating the operation of the automatically deployed safety mechanism.

DETAILED DESCRIPTION OF THE DRAWINGS

While the present invention is susceptible of embodiment in many different forms, there is shown in the drawings and will be described herein in detail, a specific embodiment, with the understanding that the present disclosure is to be considered an exemplification of the principles of the invention, and is not intended to limit the invention to the embodiment illustrated.

Automatic tissue sampling apparatus 20 is illustrated in FIG. 1, having biopsy needle system 22 already loaded therein. Automatic tissue sampling apparatus 20 includes housing 24 with cover 25. Automatic tissue sampling apparatus 20 is cocked using lever 28, which is provided with finger gripping portion 29 and thumb rest portion 30. Lever 28 is mounted for facilitated pivotal movement around pin 32, which is mounted in projection 33 of housing 24. Upon cocking, safety button 35 automatically shifts to one side and prevents button 36 from being inadvertently pressed. In order to enable button 36 to be depressed, safety button 35 must be pushed back in the opposite direction.

FIG. 2 illustrates cover 25, which, in the preferred embodiment of the invention, may be hinged to housing 24 so as to open in the manner shown. Spring catch 37 (shown in FIG. 3) holds cover 25 in the closed position, but upon moderate upward pressure to cover 25, will deflect sufficiently to release cover 25.

Central support 39 is fixably mounted generally along the longitudinal center of housing 24, and generally divides the interior of housing 24 into a forward region and a rearward region. Shaft 40 is arranged for reciprocating axial movement substantially parallel to the longitudinal axis of housing 24, and is mechanically connected to lever 28 by crank 42, which is, in turn, pivotably connected to lever 28 by pin 43 and pivotably connected to shaft 40 by pin 44. Accordingly, when lever 28 is pivoted in the direction indicated by arrow A, shaft 40 moves axially backward with respect to housing 24. Yokes 46 and 47 are each configured to be retained within housing 24 by projecting tabs, such as tab 49 of yoke 46, which are received within longitudinally extending grooves, such as groove 50. Accordingly, yokes 46 and 47 are each configured to be longitudinally, slidably moved relative to support housing 24.

Shaft 40, in the preferred embodiment of the invention, is configured to pass through yokes 46 and 47, through apertures 23 and 53, respectively. Yokes 46 and 47 are each biased forwardly, with respect to housing 24, by coil springs 55 and 56, respectively. When yoke 46 is drawn toward rear wall 26 of housing 24 during cocking (as described hereinafter), it is engaged and retained adjacent rear wall 26 by retaining member 58. Retaining member 58 is normally biased to pivot in a clockwise direction around axis 59 so that engagement portions 60 of retaining member 58 are normally biased to move upwardly relative to housing 24. Engagement portions 60, which are wedge-shaped, are driven downwardly by pins 61 (as shown in FIG. 3), until pins 61 pass the rear edges of engagement portions 60, as yoke 46 approaches rear wall 26. Once pins 61 have passed the rear edges of engagement portions 60, retaining member 58 is permitted to then rotate clockwise and pins 61 abut the rear edges of engagement portions 60, preventing yoke 46 from being driven forward under the bias of now-compressed spring 55.

FIG. 3 illustrates automatic tissue sampling apparatus 20 with yokes 46 and 47 in their fully cocked positions. Spring 62, which is weaker than either of springs 55 or 56, at one end abuts yoke 47 and at the other end abuts cross member 64. Spring 62, being at all times in a slightly compressed configuration, tends to push cross member 64 and yoke 47 apart, thereby tending to maintain shaft 40 in a forwardly drawn position with respect to, and substantially fully within, housing 24. Shaft 40 is provided with a longitudinally extending recess 65 with sharply defined end surfaces 66 and 67 as shown in FIGS. 5-11.

Yoke 47 is illustrated, in FIG. 3, in its retained position against central support 39. To draw yoke 47 against central support 39, against the bias of spring 56, when lever 28 is actuated, cross member 64 abuts the front edge of yoke 47 and forces yoke 47 backward toward central support 39. Yoke 47 is restrained in that position by retaining member 70, which is arranged for pivotal movement about axis 71. Retaining member 70 includes engagement portions 72, which engage pin 73 (see, for example, FIG. 5) in substantially the same manner as engagement portions 60 of retaining member 58 engage pins 61 of yoke 46. Retaining member 70 is, like retaining member 58, biased to pivot toward the clockwise direction (as seen in FIG. 3) and engagement portions 72 are wedge-shaped so that as yoke 47 approaches central support 39, pins 73 force retaining member 70 to pivot counter-clockwise, slightly, until pins 73 ride over and past engagement portions 72.

In order to permit the cocking of automatic tissue sampling apparatus 20, without having to overcome the combined force of both of springs 55 and 56, and as well to permit the inspection of the tissue sample once the sample has been taken (in a manner described hereinafter), the automatic tissue sampling apparatus 20 has been provided with a tissue sample inspection feature and is configured so that yokes 46 and 47 are cocked and retained against springs 55 and 56, respectively, during separate, successive actuations of lever 28. Specifically, yoke 46 is configured to normally be freely, axially movable relative to shaft 40 (aside from the biasing force of spring 55). However, catch member 74 is pivotably supported about pin 75 in a forward portion of yoke 46. Catch member 74 is biased, by spring 76, for example, in a clockwise direction upwardly away from shaft 40. However, yoke 47 is provided with rearwardly projecting pin 78 which, when yoke 47 has been drawn backward against central support 39, projects through a horizontally extending aperture (not shown) in central support 39 to depress catch member 74 downwardly toward shaft 40 so that the forwardmost edge of catch member 74 is held against the bottom of recess 65, as illustrated in FIG. 7. When lever 28 has been actuated again, the forward edge of catch member 74 abuts and is caught by the forward edge 67 of recess 65 and shaft 40, thereby pushing yoke 46 backward toward rear wall 26 and retaining member 58.

The release of yoke 46 is accomplished by pressing button 36, which pushes forward the upper end of the vertical portion of retaining member 58, simultaneously causing engagement portions 60 of retaining member 58 to pivot downwardly to remove the obstruction of pins 61, of yoke 46. Propelled by the force of spring 55, yoke 46 rapidly moves toward and impacts bumper 80 of central support 39. In addition, springs 81, mounted on the lower front face of yoke 46 come into contact with the lower face of central support 39. Due to the resistive yielding of bumper 80 and springs 81, the forward movement of yoke 46 is not instantaneously stopped, as bumper 80 and springs 81 "give" slightly, allowing yoke 46 to approach central support 39 at a predetermined minimum distance, for a short interval of time. This is necessary in order to allow secondary button 83 to come into contact with the rearward end 84 of retaining member 70. When pushed by secondary button 83, retaining member 70 pivots against the bias of spring 79 (as shown in FIGS. 5-11), causing engagement portions 72 of retaining member 70 to remove the obstruction of pins 73, of yoke 47. Accordingly, when button 36 is pressed, yokes 46 and 47 are released consecutively in rapid succession, on the order of one-one hundredth of a second. After secondary button 83 has pushed end 84 of retaining member 70, then bumper 80 and springs 81 recover and force yoke 46 back to a position where secondary button 83 is no longer in contact with end 84. This recoiling of yoke 46 enables retaining member 70 to engage pins 73 and restrain yoke 74.

As previously mentioned, the automatic tissue sampling apparatus 20 of the present invention is configured to be used with a conventional two-needle biopsy needle system 22, the general configuration of which is well known and substantially consistent from manufacturer to manufacturer. Biopsy needle system 22 is composed of two parts, first inner needle (first needle) 86 and second outer needle (removed needle) 96. First inner needle 86 consists of substantially solid shaft 87 with integrated handle 88. Angled point 89 is positioned at the end of shaft 87, opposite from handle 88, to facilitate insertion of the needle into the tissue to be sampled. Proximate to point 89, tissue holding region 90 is cut-out from shaft 87, as illustrated in FIG. 6. When biopsy needle system 22 is inserted into a tissue to be sampled, and tissue holding region 90 is exposed, a portion of the tissue moves into tissue holding region 90, and is sheared off and retained there as the desired sample.

Shaft 87 is freely insertingly received by hollow shaft 97 of second outer needle 96, with integrated handle 98. An aperture (not shown) extends through the length of handle 98. Handles 88 and 98 are typically additionally configured to be asymmetrical, particularly with tabs 92, and 99a and 99b, which have portions projecting perpendicularly from handles 88 and 98, respectively. As the length of shaft 87 exceeds the combined length of hollow shaft 97 and handle 98, point 89, at substantially all times during normal use, is exposed. The foregoing biopsy needle system description is typical of biopsy needle systems, though the particular contours, proportions configurations and handle shapes, though not handle size, may vary somewhat from one manufacturer to another. However, the principles of the automatic tissue sampling apparatus of the present invention are applicable to all.

The operation of biopsy needle system 22, to obtain and retrieve a tissue sample, is as follows. When point 89 is inserted into a tissue, first inner needle 86 and second outer needle 96 must be in the configuration shown in FIG. 5, that is, with second outer needle 86 moved forwardly relative to first inner needle 86, so that hollow shaft 97 covers tissue holding region 90 of shaft 87, but point 89 remains forwardmost and exposed.

Once first inner needle 86 and second outer needle 96 have been inserted into the tissue, first inner needle 86 is moved forward, with respect to second outer needle 96, further into that particular region of the tissue, from which a sample is to be retrieved. During this step, second outer needle 96 is to be stabilized, with respect to the patient and the tissue, for accuracy and for the comfort of the patient.

As point 89 of first inner needle 86 proceeds further into the tissue, tissue holding region 90 becomes exposed. Since the tissue is not a rigid medium, a portion of the tissue "flows" to fill in, at least partially, tissue holding region 90. To retrieve and remove the sample, second outer needle 96 is then rapidly thrust forward, relative to first inner needle 86, which, in turn, is stabilized relative to the patient and the tissue—to eventually shear off and enclose the tissue that had previously flowed into tissue holding region 90.

As illustrated in FIGS. 5 through 11, hollow shaft 97 is also provided with point 100, which is also angled to that the extreme tip 101 of point 100 is positioned, when first inner needle 86 and second outer needle 96 are aligned, on the side of the shaft 15 in which tissue holding region 90 is formed. Proper alignment of first inner needle 86 and second outer needle 96 is obtained when the projecting portions of tabs 92, 99a and 99b are aligned. Accordingly, as second outer needle 96 is moved forward relative to first inner needle 86, extreme tip 101 cuts the tissue to leave a portion of the tissue within tissue holding region 90. As second outer needle 96 continues to move forward, the tissue sample and tissue holding region 90 are covered. At this point, first inner needle 86 and second outer needle 96 have resumed the relative positions indicated by FIG. 5 and must be withdrawn from the patient together in that position, in order to prevent the tissue sample from being dislodged or contaminated by other tissue.

To accomplish such operations with precision, speed and a minimum of discomfort to the patient, using manual methods, is extremely difficult. Automatic tissue sampling apparatus 20 enables the foregoing procedure to be accomplished swiftly, with a substantially reduced level of discomfort to the patient, and with a high degree of repeatability of result from one procedure to the next.

FIGS. 5 through 11 illustrate the successive steps in the operation of the automatic tissue sampling apparatus 22. In FIG. 5, automatic tissue sampling apparatus 20 is shown in an uncocked configuration. Hollow shaft 97 of second outer needle 96 covers tissue holding region 90 of first inner needle 86. A first actuation of lever 28 causes cross member 64 to abut the front face of yoke 47, driving yoke 47 against the force of spring 56, into position to be retained by retaining member 70. This procedure draws second outer needle 96 backward relative to first inner needle 86, thus exposing tissue holding region 90. As previously described, once yoke 47 has been drawn back and retained by retaining member 70, pin 78 depresses catch member 74 against the bias of spring 76. Accordingly, when lever 28 is returned to its lowered position, returning shaft 40 to its fully forward position, catch member 74 is forced into recess 65.

A subsequent actuation of lever 28, again draws back shaft 40. However, leading edge 67 of recess 65 pushes on catch member 74 to force yoke 46 backward toward retaining member 58. The upper end of retaining member 58 simultaneously pushes button 36 backward relative to rearward projecting portion 33 of housing 24. Returning lever 28 to its initial position again places automatic tissue sampling apparatus 20 into a configuration ready for insertion of biopsy needle system 22 into the tissue to be sampled, or resampled, if required.

Due to the power and speed with which the yokes 46 and 47 are propelled forward, respectively, by springs 55 and 56, once button 36 is depressed, and in view of the hazardous nature of the biopsy needle system, it is highly desirable to provide automatic tissue sampling apparatus 20 with an automatically deployed safety mechanism to prevent actuation of automatic tissue sampling apparatus 22. The present invention is provided with such a safety mechanism, in part illustrated in FIG. 12.

FIG. 12 shows shaft 40 and safety button 35. Shaft 40 has arranged, upon an upper surface thereof, cam surface 110. Button 36 is formed in three parts, forward large diameter portion 120, central narrow portion 121, and rearward large diameter portion 122. Safety button 35 is configured as a substantially cylindrical rod having, on an upper surface thereof, an arcuate depression 111 formed thereon and extending substantially longitudinally along the axis of safety button 35. Safety button 35 is disposed parallel to the transverse axis of housing 24, for limited reciprocal movement in an aperture in projection 33. Upon the lower half of safety button 35, a recess is carved out having a depth substantially equal to the depth of cam surface 110 and having a width slightly greater than the width of shaft 40. When shaft 40 is in its forwardmost position within housing 24, as shown in FIG. 5, shaft 40 occupies the position, relative to safety button 35, indicated by the solid line button 35 in FIG. 12. As illustrated, recesses 111 and 112 are slightly offset in the transverse direction. Recess 111, when positioned relative to shaft 40 as shown in the solid line figure in FIG. 12, enables the rearward large diameter portion 122 of button 36 to pass over safety button 35, enabling button 36 to move forwardly sufficiently to pivot retaining member 58 and release yoke 46.

When lever 28 is cocked, shaft 40 is automatically moved in the direction of the arrow B in FIG. 12 and cam surface 110 forces safety button 35 to move in the direction of arrow C and thus occupy the position, relative to the shaft 40, shown as 35'. When lever 28 is returned to its lower position, shaft 40 moves forward again relative to housing 24. While recess 112 is at that time positioned over the widest part of cam surface 110, safety button 35 is held by friction in its safety position, with recess 111' offset to one side of shaft 40. Accordingly, if button 36 is depressed, the rearward large diameter portion 122 of button 36 abuts and is blocked by safety button 35. Only when safety button 35 is pushed in the direction opposite arrow C in FIG. 12, so that recess 111 again becomes aligned with shaft 40, can button 36 be fully depressed, to actuate apparatus 22.

Once biopsy needle system 22 has been positioned in the patient and into the particular tissue to be sampled, and safety button 36 moved to release button 35 automatic tissue sampling can be effectuated. FIG. 10 illustrates automatic tissue sampling apparatus 22 in a configuration only a split second after button 3 has been fully depressed. Retaining member 58 has been pivoted counter-clockwise, with engagement surfaces 60 no longer obstructing pins 61. Yoke 46 is moving rapidly toward central support 39 under the impetus of spring 55. Shaft 87 of first inner needle 86 is being propelled forward relative to hollow shaft 97 of second outer needle 96. Tissue holding region 90 is being exposed. Ultimately, yoke 46 collides with bumper 80 of central support 39 as springs 81 strike the rear face of central support 39. Bumper 80 and springs 81 are sufficiently compressed by the driving force of spring 55 that second button 83 reaches retaining member 70 and causes it to rotate counterclockwise, as illustrated in FIG. 11. Engagement surfaces 72 of retaining member 70 clear pins 73 and thus yoke 47 is propelled forward by spring 56. Second outer needle 96 is brought forward so that shaft 97 covers tissue holding region 90 of first inner needle 86. Springs 125 on yoke 47 and bumper 130 prevent yoke 47 from contacting forward wall 131.

The inner and outer needles 86 and 96 respectively, are held together to facilitate removal of biopsy needle system 22 from the tissue being sampled. Once removed from the patient, it is often desirable to inspect the tissue holding region 90, in order to determine whether a sample has been successfully taken and, if so, to enable deposit of the sample onto a microscope slide, or other appropriate receptacle. Inspection of tissue holding region 90 is easily accomplished in the present invention—by merely applying a single stroke to actuating lever 28 after it has been fired, in order to draw back second outer needle 96, as illustrated in FIG. 6. If a suitable sample has not been retrieved, after inspection, a second actuation of lever 28 draws back first inner needle 86, and places the automatic tissue sample apparatus again in a fully cocked configuration, ready for the reinsertion of biopsy needle system 22 into the tissue to be sampled.

An additional advantage of the construction of the invention, is that the provision of springs 81 and 125, and bumpers 84 and 130 prevent actual contact between yokes 46 and 47, and central support 39 and forward wall 131, which tends to reduce the noise otherwise associated with such apparatus. In addition, the deceleration produced by these elements tends to reduce the "shock" which may be felt when apparatus 20 is actuated. Noise and shock are further reduced by fabricating bumpers 84 and 130 from resilient compressible plastic or rubber material, and by fabricating yokes 46 and 47 from nylon or similar materials. By reducing noise and shock, the patient's discomfort, actual and/or perceived, during the sampling procedure, will be reduced.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An automatic tissue sampling apparatus for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrough for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement, between a first transport means forward position and a first transport means retracted position therewithin said rearward region, in a direction substantially parallel to said longitudinal axis of said housing means;

second transport means operably disposed in said forward region of said housing means for reciprocating movement between a second transport means forward position and a second transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively;

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region, first transport retaining means operably associated with said first transport means for releasably retaining said first transport means for releasably retaining said first transport means in said first transport means retracted position;

second transport retaining means operably associated with said second transport means for releasably retaining said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof;

second release means operably associated with said second transport retaining means to actuate said second transport retaining means to release said second transport means from said second transport means retracted position, when said first transport means substantially reaches said first transport means forward position thereof, to, in turn, enable said second transport means to be driven rapidly forward to said second transport means forward position thereafter, by said second biasing means;

automatic tissue sample inspection means for enabling the facilitated reorientation of said second transport means relative to said first transport means after removal of said biopsy needle system from said tissue being sampled, with the first transport means, and, in turn, said first needle, in substantially its first transport means forward position in the rearward region, with the second transport means, and, in turn, the second needle in substantially said second transport means retracted position, exposing said tissue holding region and said sampled tissue removed as a result of said tissue sampling procedure; and safety means operably associated with at least said first release means and said cocking means to preclude inadvertent actuation of at least said first release means and, in turn, said first transport means thereof, said safety means including a stop member, positionable along said first release means between a locked position in which said stop member obstructs and blocks reciprocation of said first release means upon direct access and prompting of said release means, and an opposed, unlocked position, said stop member further operably configured to be automatically positioned to physically preclude actuation of at least said first release means, by releasably immobilizing said first release means, upon actuation of said cocking means.

2. The automatic tissue sampling apparatus according to claim 1 wherein said automatic tissue sample inspection means cooperates with said second transport retaining means to releasably, yet positively maintain said second transport means in said second transport means retracted position, and said first transport means in its first transport means forward position to expose, as desired, said tissue holding region with said removed sampled tissue.

3. The automatic tissue sampling apparatus according to claim 1 wherein said automatic tissue sample inspection means comprises:

a detent member operably disposed on said first transport means, to disengage said first transport means from said cocking means; and an engagement member, operably disposed on said second transport means, to position said detent member into engagement with said cocking means, when said second transport means is in said second transport means retracted position, said cocking means and said first transport means and said second transport means being operably configured such that upon a first actuation of said cocking means after removal of said biopsy needle system from the tissue being sampled, said second transport means may be drawn to said second transport means retracted position thereof for retention by said second transport retaining means to expose said tissue holding region while said first needle is in said first transport means forward position, said engagement member being capable of placing said detent member into engagement with said cocking means, upon a second successive actuation of said cocking means to reposition said first transport means into said first transport means retracted position thereof for retention by said first transport retaining means, thereby enabling tissue resampling by said apparatus, 4. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrough for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement, between a first transport means forward position and a first transport means retracted position therewithin said rearward region, in a direction substantially parallel to said longitudinal axis of said housing means;

second transport means operably disposed in said forward region of said housing means for reciprocating movement between a second transport means forward position and a second transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively;

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region, said cocking means including a pivotably mounted lever member, operably disposed externally to said housing means, to enable facilitated, leveraged, cocking of said first and second biasing means, and, in turn, said first and second transport means, respectively;

first transport retaining means operably associated with said first transport means for releasably retaining said first transport means in said first transport means retracted position;

second transport retaining means operably associated with said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof; and second release means operably associated with said second transport retaining means to actuate said second transport retaining means to release said second transport means from said second transport means retracted position, when said first transport means substantially reaches said first transport means forward position thereof, to, in turn, enable said second transport means to be driven rapidly forward to said second transport means forward position thereafter, by said second biasing means.

5. The automatic tissue sampling apparatus according to claim 4 further comprising:

automatic tissue sample inspection means for enabling the facilitated reorientation of said second transport means relative to said first transport means after removal of said biopsy needle system from said tissue being sampled, with the first transport means, and, in turn, said first needle, in substantially its first transport means forward position in the rearward region, with the second transport means, and, in turn, the second needle in substantially the second transport means retracted position, exposing said tissue holding region and said sampled tissue removed as a result of said tissue sampling procedure.

6. The automatic tissue sampling apparatus according to claim 5 wherein said automatic tissue sample inspection means cooperates with said second transport retaining means to releasably, yet positively maintain said second transport means in said second transport means retracted position, and said first transport means in its forward position to expose, as desired, said tissue holding region with said removed sampled tissue.

7. The automatic tissue sampling apparatus according to claim 5 wherein said automatic tissue sample inspection means comprises:

a detent member operably disposed on said first transport means, to disengage said first transport means from said cocking means, and an engagement member, operably disposed on said second transport means, to position said detent member into engagement with said cocking means, when said second transport means is in said second transport means retracted position, said cocking means and said first transport means and second transport means being operably configured such that upon a first actuation of said cocking means after removal of said biopsy needle system from the tissue being sampled, said second transport means may be drawn to said second transport means retracted position thereof for retention by said second transport retaining means to expose said tissue holding region while said first needle is in said first transport means forward position, said engagement member being capable of placing said detent member into engagement with said cocking means, upon a second successive actuation of said cocking means to reposition said first transport means into said first transport means retracted position thereof for retention by said first transport retaining means, thereby enabling tissue re-sampling by said apparatus.

8. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrough for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement between a first transport means forward position and a first transport means retracted position therewithin said rearward region, in a direction substantially parallel to said longitudinal axis of said housing means;

second transport means operably disposed in said forward region of said housing means for reciprocating movement between a second transport means forward position and a transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively;

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region;

first transport retaining means operably associated with said first transport means for releasably retaining said first transport means in said first transport means retracted position;

second transport retaining means operably associated with said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof;

second release means operably associated with said second transport retaining means to actuate said second transport retaining means to release said second transport means from said second transport means retracted position, when said first transport substantially reaches said first transport means forward position thereof, to, in turn, enable second transport means to be driven rapidly forward to said second transport means forward position thereafter, by said second biasing means; and safety means operably associated with said first release means and said cocking means to preclude inadvertent actuation thereof, said safety means operably and automatically deployed to preclude actuation of at least said first release means, upon actuation of said cocking means, said safety means including a stop member, operably configured to be automatically positioned to physically preclude actuation of at least said first release means, by releasably immobilizing said first release means, upon actuation of said cocking means.

9. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrugh for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement, between a first transport means forward position and a first transport means retracted position therewithin said rearward region, in a direction substantially parallel to said longitudinal axis of said housing means;

second transport means operably disposed in said forward region of said housing means for reciprocating movement between a second transport means forward position and a second transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively:

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region;

first transport retaining means operably associated with said first transport means for releasably retaining said first transport means in said first transport means retracted position;

second transport retaining means operably associated with said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof;

second release means operably associated with said second transport retaining means to actuate said second transport retaining means to release said second transport means from said second transport means retracted position, when said first transport means substantially reaches said first transport means forward position thereof, to, in turn, enable said second transport means to be driven rapidly forward to said second transport means forward position thereafter, by said second biasing means; and automatic tissue sample inspection means for enabling the facilitated reorientation of said second transport means relative to said first transport means after removal of said biopsy needle system from said tissue being sampled, with the first transport means, and, in turn, said first needle, in substantially its first transport means forward position in the rearward region, with the second transport means, and, in turn, said second needle, in substantially said second transport means retracted position, exposing said tissue holding region and said sampled tissue removed as a result of said tissue sampling procedure, said automatic tissue sample inspection means including a detent member operably disposed on said first transport means, to disengage said first transport means from said cocking means, and an engagement member, operably disposed on said second transport means, to position said detent member into engagement with said cocking means, when said second transport means is in said second transport means retracted position, said cocking means and said first transport means and said second transport means being operably configured such that upon a first actuation of said cocking means after removal of said biopsy needle system from the tissue being sampled, said second transport means may be drawn to said second transport means retracted position thereof for retention by said second transport retaining means to expose said tissue holding region while said first needle is in said first transport means forward position, said engagement member being capable of placing said detent member into engagement with said cocking means, upon a second successive actuation of said cocking means to reposition said first transport means into said first transport means retracted position thereof for retention by said first transport retaining means, thereby enabling tissue re-sampling by said apparatus.

10. The invention according to claim 9 in which said cocking means are actuatable a first time to orient said second transport means to said biased, second transport means retracted position, said cocking means being reactuatable a second, successive time to orient said first transport means to said biased, first transport means retracted position, for subsequent projection into said tissue being sampled.

11. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrough for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement, between a first transport means forward position and a first transport means retracted position therewithin said rearward region, in a direction substantially parallel to said longitudinal axis of said housing means;

second transport means operably disposed in said forward region of said housing for reciprocating movement between a second transport means forward position and a second transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively;

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region, said cocking means being actuatable a first time to orient said second transport means to said biased, second transport means retracted position, said cocking means being reactuatable a second, successive time to orient said first transport means to said biased, first transport means retracted position, for subsequent projection into said tissue being sampled;

first transport retaining means operably associated with said first transport means for releasably retaining said first transport means in said first transport means retracted position;

second transport retaining means operably associated with said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof;

second release means operably associated with said second transport retaining means to actuate said second transport retaining means to release said second transport means from said second transport means retracted position, when said first transport means substantially reaches said first transport means forward position thereof, to, in turn, enable said second transport means to be driven rapidly forward to said second transport means forward position thereafter, by said second biasing means; and automatic tissue sample inspection means for enabling the facilitated reorientation of said second transport means relative to said first transport means after removal of said biopsy needle system from said tissue being sample, with the first transport means, and, in turn, said first needle, in substantially its first transport means forward position in the rearward region, with the second transport means, and, in turn, the second needle in substantially said second transport means retracted position, exposing said tissue holding region and said sampled tissue removed as a result of said tissue sampling procedure.

12. The automatic tissue sampling apparatus according to claim 1 wherein said housing means comprises:
a substantially solid-walled, generally continuous apparatus enclosure having a substantially rectangular cross-sectional configuration for substantially enclosing the reciprocating portions of said automatic tissue sampling apparatus and to protect same from dirt, moisture and the like, as well as to provide audio isolation of said moving portions to reduce noise produced during operation of said automatic tissue sampling apparatus.

13. The automatic tissue sampling apparatus according to claim 12, wherein said enclosure comprises:
two oppositely disposed sidewalls extending substantially parallel to said longitudinal axis of said housing means, each of said sidewalls having a forward end and a rearward end;
a forward wall, extending substantially parallel to said transverse axis of said housing means, operably connecting said forward ends of each of said sidewalls;
a rearward wall, extending substantially parallel to said transverse axis of said apparatus housing, operably connecting said rearward ends of each of said sidewalls;
a bottom wall, extending substantially parallel to said longitudinal axis, operably connecting said forward and rearward walls and said sidewalls;
an openable cover member disposed opposite said bottom wall for permitting placement and removal of said biopsy needle system and enclosure of same in a substantially fully enclosed environment; and
a central support member, operably positioned between said sidewalls, substantially centrally between said forward and rearward walls.

14. The automatic tissue sampling apparatus according to claim 13, wherein said first transport means comprises:
a first yoke member operably configured to be longitudinally and slidably retained between said sidewalls, said rearward wall, and said central support member, and operably configured to receive and retain said first handle of said first needle.

15. The automatic tissue sampling apparatus according to claim 14, wherein said second transport means comprises:
a second yoke member operably configured to be longitudinally and slidably retained between said forward wall and said central support member, and operably configured to receive and retain said second handle of said second needle.

16. The automatic tissue sampling apparatus according to claim 15, wherein said first biasing means comprises:
a compressed spring operably positioned between said rearward wall and said first yoke member.

17. The automatic tissue sampling apparatus according to claim 16, wherein said second biasing means comprises:
a compressed spring operably positioned between said central support member and said second yoke member.

18. The automatic tissue sampling apparatus according to claim 17, wherein said cocking means comprises:
a shaft, extending substantially parallel to said longitudinal axis, operably disposed for reciprocating movement parallel to said longitudinal axis, and having two ends, a first of said two ends extending through an aperture in said rearward wall;
a pivotable lever, operably and pivotably disposed upon said rearward wall for pivotal movement around an axis extending substantially parallel to said transverse axis, said lever further being operably associated with said first end of said shaft such that when said lever is pivotally moved, said shaft is moved rearwardly;
a cross member operably disposed upon a second end of said shaft, opposite to said first end, so as to abut a forward face of said second yoke member when said lever is actuated and said second yoke member is in said second transport means forward position thereof, so as to draw said second yoke member toward said second transport means retracted position.

19. The automatic tissue sampling apparatus according to claim 18, wherein said cocking means further comprises:
biasing means operably disposed between said cross member and said second transport means for normally biasing said shaft in a forwardmost position relative to said housing means.

20. The automatic tissue sampling apparatus according to claim 11 wherein said first and second biasing means are operably disposed and configured to function substantially independently of each other.

21. The automatic tissue sampling apparatus according to claim 11, in which the invention further comprises:

safety means operably associated with at least said first release means and said cocking means to preclude inadvertent actuation of at least said first release means and, in turn, said first transport means thereof.

22. The automatic tissue sampling apparatus according to claim 21, wherein said safety means comprises:

a stop member, operably configured to be automatically and removably positioned to physically preclude actuation of at least said first release means, upon actuation of said cocking means.

23. An automatic tissue sampling apparatus for use with a biopsy needle system of the kind including a first needle having a shaft member and two ends, a first handle disposed at one end of the shaft member, a cutting point disposed at the other end of the shaft member, and a tissue holding region positioned between the cutting point and the first handle; and a second needle having a hollow shaft and two ends, a cutting point disposed at one end of the hollow shaft, a second handle with a passageway arranged therethrough for telescopic receipt and reciprocation of said first needle therewithin, and particularly for the automated and facilitated handling and operation of said biopsy needle system during a biopsy procedure, said automatic tissue sampling apparatus comprising:

housing means having a forward region, a rearward region, a longitudinal axis and a transverse axis;

first transport means operably disposed in said rearward region of said housing means, for reciprocating movement between a first transport means forward position and a first transport means retracted position therewithin said rearward region, in a direction substantially parallel to said longitudinal axis of said housing means;

second transport means operably disposed in said forward region of said housing means for reciprocating movement between a second transport means forward position and a second transport means retracted position therewithin said forward region, in a direction substantially parallel to said longitudinal axis of said housing means, said first transport means and said second transport means being configured to receive and longitudinally move, in said reciprocating directions, said first handle of said first needle and said second handle of said second needle, respectively;

first biasing means operably arranged in said rearward region of said housing means for biasing said first transport means forwardly toward said first transport means forward position;

second biasing means, operably arranged in said forward region of said housing means, for biasing said second transport means forwardly toward said second transport means forward position;

cocking means, integrally and operably associated with said first transport means and said second transport means, for drawing said first transport means, and, in turn, said first needle, rearwardly into said first transport means retracted position thereof, within said rearward region, and for drawing said second transport means, and, in turn, said second needle, rearwardly into said second transport means retracted position thereof, within said forward region;

said cocking means including a single axially movable cocking shaft member operably arranged to extend through each of said first and second transport means and through said first and second biasing means, in parallel, spaced relation to said biopsy needle system, said cocking shaft member being operably associated with each of first and second transport means for drawing said first transport means to said first transport means retracted position and said second transport means to said second transport means retracted position, upon actuation of said cocking means;

first transport retaining means operably associated with said first transport means for releasably retaining said first transport means in said first transport means retracted position;

second transport retaining means operably associated with said second transport means for releasably retaining said second transport means in said second transport means retracted position;

first release means operably associated with said first transport retaining means to actuate said first transport retaining means to release said first transport means from said first transport means retracted position to, in turn, enable said first transport means to be driven rapidly forward by said first biasing means, toward said first transport means forward position thereof;

second release means operably associated with said second transport retaining means to actuate said second transport retaining means to release said second transport means from said second transport means retracted position, when said first transport means substantially reaches said first transport means forward position thereof, to, in turn, enable said second transport means to be driven rapidly forward to said second transport means forward position thereafter, by said second biasing means; and automatic tissue sample inspection means for enabling the facilitated reorientation of said second transport means relative to said first transport means after removal of said biopsy needle system from said tissue being sampled, with the first transport means, and, in turn, said first needle, in substantially its first transport means forward position in the rearward region, with the second transport means, and, in turn, the second needle in substantially said second transport means retracted position, exposing said tissue holding region and said sampled tissue removed as a result of said tissue sampling procedure.

* * * * *

UNITED STATES PATENT AND TRADEMARK OFFICE
CERTIFICATE OF CORRECTION

PATENT NO. : 5,284,156
DATED : February 8, 1994
INVENTOR(S) : John B. Schramm; Anton Mittermeier It is certified that error appears in the above-indentified patent and that said Letters Patent is hereby corrected as shown below:

Col. 5, Line 16  Delete "first, and insert instead -- second --.

Col. 11, Line 16  Delete "removed", and insert instead -- second --.

Col. 19, Line 65  After "transport", insert -- means --.

Col. 20, Line 24  Delete "therethrugh", and insert instead -- therethrough --.

Signed and Sealed this

Twenty-fifth Day of April, 1995

Attest:

BRUCE LEHMAN

Attesting Officer     Commissioner of Patents and Trademarks